US006960338B2

(12) United States Patent
Li et al.

(10) Patent No.: US 6,960,338 B2
(45) **Date of Patent: *Nov. 1, 2005**

(54) AMINO ACID FREE STABLE ALUMINUM/ ZIRCONIUM ANTIPERSPIRANT SOLUTION

(75) Inventors: Zijun Li, Westfield, NJ (US); Jawahar Chunilal Parekh, Livingston, NJ (US)

(73) Assignee: Reheis, Inc., Berkeley Heights, NJ (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/185,298

(22) Filed: Jun. 28, 2002

(65) Prior Publication Data

US 2004/0001795 A1 Jan. 1, 2004

(51) Int. Cl.[7] .......................... A61K 7/32; A61K 7/34; A61K 7/38; A61K 7/00

(52) U.S. Cl. .......................... 424/65; 424/66; 424/68; 424/400; 424/401

(58) Field of Search .......................... 424/65, 66, 68, 424/400, 401

(56) References Cited

U.S. PATENT DOCUMENTS

| | | | |
|---|---|---|---|
| 3,981,986 A | | 9/1976 | Rubino |
| 4,775,528 A | | 10/1988 | Callaghan et al. |
| 5,114,705 A | | 5/1992 | Callaghan et al. |
| 5,225,187 A | | 7/1993 | Carmody |
| 5,486,347 A | | 1/1996 | Callaghan et al. |
| 5,589,196 A | | 12/1996 | Callaghan et al. |
| 5,908,616 A | | 6/1999 | Parekh et al. |
| 5,939,057 A | | 8/1999 | Provancal et al. |
| 5,955,064 A | | 9/1999 | Giovanniello et al. |
| 6,066,314 A | | 5/2000 | Tang et al. |
| 6,074,632 A | | 6/2000 | Shen |
| 6,126,928 A | | 10/2000 | Swaile |
| 6,451,296 B1 | * | 9/2002 | Li et al. ...................... 424/66 |

FOREIGN PATENT DOCUMENTS

| | | |
|---|---|---|
| CH | 527-218 | 8/1972 |
| EP | 0 295 070 | 12/1988 |
| EP | 0653203 A1 | 5/1995 |
| WO | PCT/AU01/0080 | 8/2001 |
| WO | WO 01/56539 A1 | 8/2001 |
| WO | WO 02/34211 A2 | 5/2002 |
| WO | WO 02/34223 A2 | 5/2002 |

OTHER PUBLICATIONS

Antiperspirant and Deodorants—K. Laden, et al. vol. 7 Cosmetic Science and Technology; Chap 5 pp 137–139, 146, 147 and Chap 6 pp 165–167, 180, 183.

Zirconium Aluminum in Antiperspirant—R. Bertram, et. al. SöFW Journal, Oct. 1997 p 664.

* cited by examiner

*Primary Examiner*—Shelley A. Dodson
(74) *Attorney, Agent, or Firm*—Arthur J. Plantamura

(57) ABSTRACT

An amino acid free stable aluminum zirconium polyhydric alcohol aqueous solution having a high anhydrous antiperspirant solid concentration and a high percentage of low molecular weight aluminum species, i.e., containing 60% or more of band IV peak area based on high pressure liquid chromatography, is prepared by adding a zirconium salt to an aqueous polyhydric alcohol solution of a basic aluminum chloride.

8 Claims, 1 Drawing Sheet

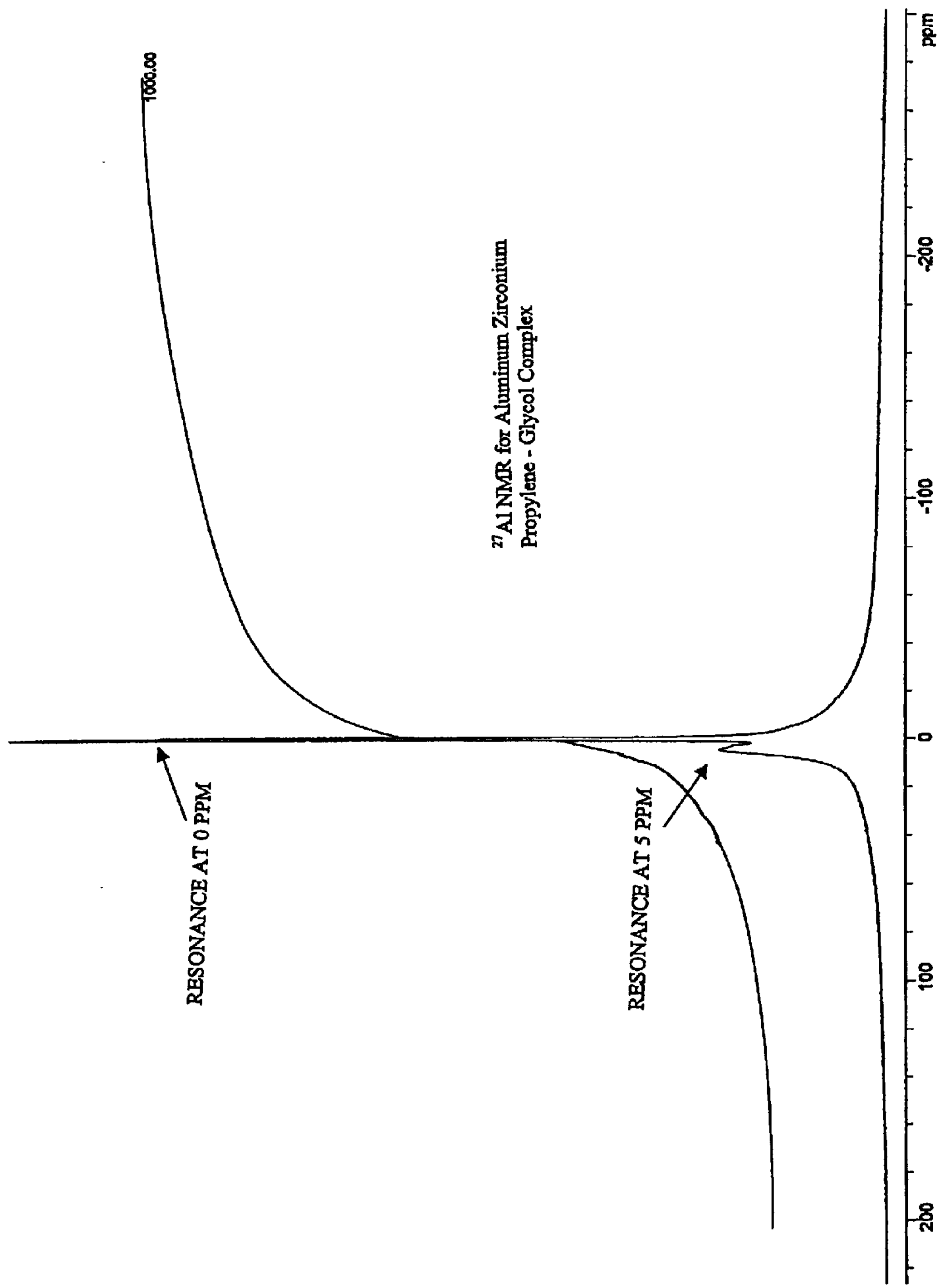
27Al NMR for Aluminum Zirconium
Propylene - Glycol Complex
RESONANCE AT 0 PPM
RESONANCE AT 5 PPM
ppm
-200
-100
0
100
200

AMINO ACID FREE STABLE ALUMINUM/ ZIRCONIUM ANTIPERSPIRANT SOLUTION

This invention relates to stable aluminum-zirconium antiperspirant solutions of enhanced efficacy and to methods of making them.

BACKGROUND OF THE INVENTION

Basic aluminum halides, or aluminum halohydrates, are well known antiperspirant compositions. The addition of zirconium compounds to aluminum complexes generally enhances the efficacy of the antiperspirants because of the depolymerization of aluminum species in the presence of zirconium. As the concentration of zirconium increases, more monomeric and low molecular weight aluminum cations are formed, and changes in the structures of the polymers are also observed.

Higher charge/size ratios and faster hydrolysis rates for $Zr^{4+}$ ion hydrolysis complexes also account for improvements in aluminum-zirconium antiperspirants over the use of antiperspirants containing solely aluminum. However, the presence of zirconium species decreases the stability of the corresponding aluminum-zirconium antiperspirant solutions because zirconium hydrolysis species precipitate at a relative lower pH than the corresponding aluminum species. Glycine is generally added in order to stabilize the aluminum-zirconium antiperspirant solutions. It is believed that the complexation between zirconium and glycine stabilizes the aluminum-zirconium antiperspirant solutions. The presence of too much glycine, however, tends to decrease the antiperspirant efficacy of aluminum-zirconium antiperspirants. Further, the use of amino acids, such as glycine, introduces an additional relative expense to the preparation of the antiperspirant.

Current commercial aluminum-zirconiun-glycine salts (ZAG) and compositions contain glycine, with the Zr:glycine weight ratio being approximately 1:1. US patents disclosing composition of this kind include U.S. Pat. Nos. 4,775,528; 5,114,705; 5,225,187; 5,486,347; 5,589,196; 5,955,064; 6,066,314; EP 0 653 203 A1 with respect to antiperspirant compositions containing polyhydric alcohols.

U.S. Pat. No. 6,074,632 disclose antiperspirant salts in stabilized aqueous polyhydric alcohol solutions. The polyhydric alcohols have from 3–6 carbon atoms and 3–6 hydroxyl groups. The highest concentration of Al—Zr active in the solution has about 36% anhydrous solid.

U.S. Pat. No. 5,939,057 presents a product comprising a clear polyhydric alcohol solution of about 20 to 50% by weight of active, about 2 to 16% by weight water, and a glycine to zirconium ratio of about 1.3:1 to about 4:1. The product of enhanced efficacy aluminum-zirconium chlorohydrate glycinate has an HPLC peak 4 to 3 ratio of at least 0.7. The process of making such product involves making an activated aluminum antiperspirant solution by diluting and heating, followed by addition of zirconium hydroxyl chloride glycinate solution and polyhydric alcohol, and rapidly evaporating the water under vacuum. Such process is lengthy and not economical.

WO 01/56539 A1 involves a process of making Al—Zr active salts in polyhydric alcohol solutions by the direct react of aluminum salt aqueous solution with zirconium oxychloride crystal, a polyhydric alcohol, aluminum metal and optionally an amino acid buffer. The reaction temperature is maintained at about 100° C. to 140° C. to provide an Al—Zr complex in the polyhydric alcohol at a concentration of about 20 to 45% A.S. The amount of polyhydric alcohol is 20 to 70% by weight of the final antiperspirant solution. The product has a HPLC Band III and IV of at least 60%, and $Al^a$ is from 25 to 55% by Ferron analysis. The invention involved a direct process. The product does not include an antiperspirant active with lower polyhydric alcohol content of less than 20% by weight.

WO 02/34211 A2 comprise aluminum zirconium salts having a metal to chloride molar ratio in the range of 0.9–1.2:1 and glycine to zirconium molar ratio greater than 1.3:1. It is necessary that glycine be present in order to obtain the desired product.

WO 02/34223 A2 discloses enhanced efficacy aluminum zirconium antiperspirant salt compositions have a metal to chloride ratio of about 0.9 to about 1.0. Such compositions exhibit an HPLC peak 5 area content of about 33% to at least 55%. However, an amino acid has to be present to afford the enhanced efficacy antiperspirant salts.

From the status of the known prior art, it is regarded as desirable to provide a stable aluminum-zirconium antiperspirant having a high active content and easy to make that does not require the inclusion of amino acid, such as glycine.

SUMMARY OF THE INVENTION

The present invention provides a novel aluminum-zirconium (Al—Zr) composition comprising, in percent by anhydrous solid (A.S.), about 20–55% antiperspirant active, about 20 to 75% by weight of water, about 1 to 20% by weight of a polyhydric alcohol, preferably an alcohol that has at least two carbon atoms and at least two hydroxyl groups. The invention provides a method of making stable antiperspirant solutions of aluminum-zirconium of high efficacy, that is, solutions that have a high proportion of lower molecular weight aluminum species, and in which the addition of amino acid stabilizers is not a requirement. The aluminum to zirconium ratio of the solutions contemplated by the invention is of the order of about 0.8 to about 10.

In accordance with the method of the present invention, aqueous aluminum salt solutions made from an aluminum salt and water and including a polyhydric alcohol, preferably of the kind that has at least two carbon atoms and at least two hydroxyl groups, is mixed with a zirconium oxychloride salt. The resultant mixture is reacted for a suitable period, for example, from about 20 minutes to about 4 hours, preferably about 30 minutes to one hour. The reaction proceeds at room temperature and can be expedited with increased temperatures, up to about 105° C., and is then filtered to obtain a clear, generally colorless solution.

BRIEF DESCRIPTION OF THE DRAWING

FIG. 1 is a $^{27}$Al NMR chromatogram of a solution obtained according to the present invention.

DETAILED DESCRIPTION OF THE INVENTION

The present process mixes a basic aluminum salt polyhydric alcohol solution with a zirconium compound, preferably zirconium oxychloride salt, at a wide range of temperatures from room temperature up to 105° C. for a suitable period of time i.e. until a substantially clear solution is obtained.

The stable solution may be prepared also by mixing a basic aluminum salt solution with a polyhydric alcohol and then reacting the mixture with a zirconium salt. Alternatively, the solution may be obtained by first mixing the zirconium salt solution with a polyhydric alcohol and then adding this solution to a basic aluminum salt.

The preferred solutions contain 40% or more of anhydrous solids and have a low polyhydric alcohol content of less than 20%. Solutions of this kind are less "tacky"; easy to make; contain a high content of low molecular weight aluminum species; and are stable without the requirement of adding relatively expensive amino acids, such as glycine.

Aqueous basic aluminum polyhydric alcohol solutions are made from aluminum salt, such as aluminum chloride in water, which contains a polyhydric alcohol. Aluminum powder is slowly added and the reaction mixture is heated for about 1–2 hours and filtered to obtain a clear, generally colorless solution.

The preferred basic aluminum salt polyhydric alcohol solution has the formula:

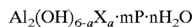

$$Al_2(OH)_{6-a}X_a \cdot mP \cdot nH_2O$$

wherein a has a numerical value from about 0.5 to about 3, X is chloride, bromide, iodine, nitrate, perchlorate or sulfate; P represents polyhydric alcohol, and m has a numerical number of about 0.1 to about 2, n has a numerical value of about 0.5 to about 4.

The concentration of the aluminum salt in the solution in percent by weight is in the range of about 20 to about 55%, preferably from about 35 to about 50%, and most preferably from about 40 to about 45%.

The amount of polyhydric alcohol in the above solution is adjusted so that the desired aluminum-zirconium antiperspirant solution contains less than 20% by weight of polyhydric alcohol.

Zirconium oxychloride is then added to the aluminum solution, the mixture is heated to about 90° C. for 0.5 to 2 hours and is then filtered.

The resultant aluminum-zirconium antiperspirant solutions contain high anhydrous solid active in the range of about 20 to about 55%, preferably from about 35% to about 55%, and most preferably from about 40% to about 50% of the anhydrous solid.

The degree of polymerization of aluminum complexes can be determined by the high performance liquid chromatography (HPLC). The highest molecular weight Al species are eluted first, designated as Band I. Bands II and III designate intermediate molecular weight Al complexes. Band IV designates the lowest molecular weight Al complexes, including monomers and dimers. The relative area of one or more peaks is determined in order to characterize the distribution of polymeric species in the aluminum complexes formed.

The aqueous solutions of hydrated aluminum chloride of 10–20% concentration exhibit chromatograms with a single aluminum solute peak designated as Band IV. When 50% by weight basic aluminum chloride is prepared by an oxidation-reduction reaction, the monomeric aluminum species represented by Band IV gradually decrease from an initial value of about 100% to less than 5% when the reaction is complete. When a 2% by weight solution of aluminum chloride is injected, two peaks are observed. The aluminum containing species is in Band IV and none are in Band V, which is believed to contain small size, non-aluminum species such as chloride.

The present invention provides a method of making stable antiperspirant solutions of aluminum and zirconium having high efficacy, i.e., having a high proportion of lower molecular weight aluminum species, while permitting the exclusion of amino acid stabilizer such as glycine.

The resultant high solid content antiperspirant solution contains high amounts of Band IV or low molecular weight aluminum complexes. The percent of Band IV peak area is desirably in the range from about 30 to about 75%, preferably from about 40 to about 65%, and more preferably from about 50 to about 60%.

A Phenominex column is used to obtain the HPLC chromatograph. A sample of a 2% by weight solution of Al is filtered through a 45-micron filter and chromatographed within 5 minutes using a 0.01N nitric acid solution as the mobile phase.

$^{27}$Al nuclear magnetic resonance (NMR) is employed to determine the structure of aluminum in the Al—Zr antiperspirant. $^{27}$Al NMR spectra of the solutions were collected using a Tecmag Libra System SDS 360-1. The data were collected from about +160 to −160 ppm. The indication is the presence of large amounts of low molecular weight aluminum species.

The weight percentage of antiperspirant salt is indicated herein as percent of anhydrous solid (% A.S.), which excludes any bound water and glycine. This is calculated in accordance with the following equation:

$$\%\ A.S. = \%\ Al[26.98x+17.01(3x-1)+35.453]/26.98x$$

wherein x=Al/Cl ratio; or $$\%\ A.S. = \%\ Al\{26.98y+92.97+17.01[3y+4-(y+1)/z]+35.453(y+1)/z\}/26.98y$$

wherein y=Al/Zr ratio and z=metal/Cl ratio.

The following comparison illustrates the difference in the calculation of antiperspirant salt between the present method and the previous standard industry method.

| SALT | STANDARD METHOD | PRESENT METHOD |
|---|---|---|
| ACH (solution) | 50% (w/w) | 40.8% (A.S.) |
| Al—Zr-Gly (solution) | 50% (w/w) | 38.5% (A.S.) |
| Component A* | — | 40% (A.S.) |
| Al—Zr—P (see Example 2) | — | 50.8% (A.S.) |

*see below - under "Preparation of Basic Aluminum Chloride in Propylene Glycol Solutions"

Suitable polyhydric alcohols for use in the present invention have at least two carbon atoms, and preferably, from 2 to 12 carbon atoms to which at least two hydroxyl groups are attached. Suitable examples include propylene glycol, butylene glycol, 1,3-butane-diol, 1,4-butane-diol, diethylene glycol, dipropylene glycol, tripropylene glycol, glycerin, sorbitol and the like. The amount of polyhydric alcohol employed is adjusted so that the final antiperspirant solution contains less than 20% by weight of polyhydric alcohol.

The aluminum-zirconium active formed is monitored by HPLC, which separates the polymeric aluminum species by size. Thus larger, high molecular weight molecules elute in Band I and Bands II–IV have progressively smaller species. At least 60% of the aluminum species corresponds to Bands III and IV. Such solutions are much more effective as antiperspirants than when higher molecular weight Al polymer species are present.

The invention will be further described in the following Examples. In the Examples, parts are by weight. Anhydrous solid content is given as % A.S.

Preparation of Basic Aluminum Chloride in Propylene Glycol Solutions

Component A 367 parts of aluminum chloride, 332 parts of water and 200 parts of propylene glycol (PG) were placed in a conical flask with a reflux condenser, and the reaction mixture was heated to 100° C. 101 parts of aluminum powder was added over a period of 50 minutes. After one hour the reaction mixture was filtered and the clear solution was collected.

Chemical analysis of this solution was: % Al, 12.23; % Cl, 8.5; % PG, 20.5.

HPLC data: % Band I, 17.4; % Band II, 57.8; % Band III, 11.1; % Band IV, 13.7.

Components B, C, D and F were prepared in a similar fashion. The results are set forth below in Table I.

TABLE I

| | % Al | % Cl | % PG | % Band I | % Band II | % Band III | % Band IV |
|---|---|---|---|---|---|---|---|
| Component B | 12.84 | 15.25 | 5.0 | 0.7 | 22.3 | 16.4 | 60.6 |
| Component C | 11.52 | 9.08 | 17.7 | 0.0 | 78.3 | 6.6 | 15.1 |
| Component D | 11.97 | 7.82 | 26.3 | 18.6 | 54.6 | 14.6 | 12.2 |
| Component E | 11.10 | 9.14 | 9.7 | 0.0 | 73.0 | 10.9 | 6.1 |
| Component F | 11.24 | 10.17 | 0 | 0 | 60.54 | 13.58 | 25.88 |
| Component G | 11.18 | 8.88 | 0 | 0 | 72.94 | 12.27 | 14.79 |

EXAMPLE 1

133 parts of component A was mixed with 138 parts of zirconium oxychloride. The mixture was heated to 90° C. for 30 minutes and was filtered. A clear colorless solution was obtained. The solution was stable after one year.

Chemical analysis: % Al, 5.99; % Zr, 13.96; % Cl, 15.58; % PG, 9.65; % A.S., 49.6.

Ferron analysis: 46.6% $Al^a$; HPLC result: 64.5% Band IV $^{27}Al$ NMR is shown in the FIG. 1.

EXAMPLES 2–9

The procedure of Example 1 was followed, and results obtained are summarized in Table II. In each of the Examples 2–9 summarized in Table II, Components B through G listed in Table I were used, as shown in column 1 of Table II.

TABLE II

| | Ex. | % Al | % Zr | % Cl | % gly | % PG | % A.S. | % Band IV | % $Al^a$ |
|---|---|---|---|---|---|---|---|---|---|
| D | 2 | 6.19 | 14.2 | 15.58 | — | 13.20 | 50.8 | 63.2 | 52.2 |
| D | 3 | 6.06 | 12.12 | 14.25 | — | 14.18 | 45.9 | 63.7 | 54.2 |
| E | 4 | 6.69 | 9.16 | 13.00 | — | 9.75 | 42.0 | 60.2 | 50.0 |
| B | 5 | 8.03 | 3.24 | 12.60 | — | 3.00 | 35.5 | 68.8 | 45.5 |
| C | 6 | 6.40 | 11.05 | 14.03 | 2.84 | 9.12 | 44.9 | 61.4 | 58.5 |
| F | 7 | 7.98 | 4.18 | 10.47 | 5.10 | — | 35.7 | 49.0 | — |
| E | 8 | 6.50 | 8.90 | 12.63 | 7.14 | 4.32 | 40.8 | 66.9 | 53.9 |
| G | 9 | 6.11 | 10.51 | 13.00 | 6.56 | — | 42.6 | 64.6 | 58.3 |

Examples 2–5 showed good stability, i.e., had a stability of at least 6 months without gelling. It is seen that in the presence of glycine and the absence of propylene glycol, higher concentration Al—Zr solutions tend to gel. The solution of Example 6 containing glycine as well as propylene glycol gelled after 4 months. The solution of Example 7 omitting the PG, gelled in 3 months. The solution of Example 8 with higher amounts of glycine, gelled in two months. The solution of Example 9 with less glycine than example 8, contained no PG gelled in one month.

$^{27}Al$ NMR spectra were collected and are set fourth below:

| Sample | Resonance Line Area at ~0 ppm | Resonance Line Area at ~5 ppm |
|---|---|---|
| Example 1 | 23.6% | 76.4% |
| Example 2 | 21.1% | 78.9% |
| Example 3 | 15.0% | 85.0% |
| Example 4 | 14.7% | 85.3% |
| Example 5 | 11.7% | 88.3% |

Irritancy test for the solution of present invention indicates the solution is not irritating to human skin.

The present polyhydric alcohol solutions of aluminum-zirconium complexes made in accordance with the invention are highly desirable for enhanced efficacy antiperspirants that are not tacky and are suitable for clear antiperspirant products, as well as stick products.

Although the present invention has been described in terms of specific embodiments, the invention is not meant to be so limited. Various changes can be made to the composition and proportions used while still obtaining the benefits of the invention. Thus the invention is only to be limited by the scope of the appended claims.

What is claimed:

1. An amino acid free stable aluminum-zirconium aqueous solution comprising, in percent by anhydrous solid, about 20 to 55% antiperspirant active, about 20 to 75% by weight water and about 1 to 20% by weight polyhydric alcohol having at least 2 carbon atoms and at least two hydroxyl groups and having an aluminum to zirconium atomic ratio of about 0.8 to 10 and a metals to chloride atomic ratio of about 0.8 to 2.1.

2. The solution according to claim 1, comprising about 35 to 45% anhydrous solid aluminum zirconium antiperspirant active, about 35 to 55% by weight water, and about 10 to 15% by weight polyhydric alcohol and a metals to chloride ratio of about 0.8 to about 1.2 and an aluminum to zirconium ratio from about 2.0 to about 9.0.

3. The solution according to claim 1, wherein said polyhydric alcohol is propylene glycol.

4. The solution according to claim 2, wherein said the aluminum zirconium antiperspirant solution has a HPLC Band IV area of about 20 to 75%.

5. The composition according to claim 4, wherein said the stable solution has a HPLC Band IV area of 45 to 65%.

6. The antiperspirant composition according to claim 2, wherein the solution has $^{27}Al$ NMR spectrum wherein 100% of the total area is contained in the chemical shift of about 0 to about 10 ppm.

7. A dried antiperspirant solution according to claim 1.

8. The solution of claim 1 in which the polyhydric alcohol has two carbon atoms and two hydroxyl groups.

* * * * *